United States Patent
Crook et al.

(10) Patent No.: US 8,382,811 B2
(45) Date of Patent: Feb. 26, 2013

(54) TRIPLE LEAD BONE SCREW

(75) Inventors: David Crook, Mineola, TX (US); Peter Harris, Boca Raton, FL (US); Chester Sharps, Manakin-Sabot, VA (US)

(73) Assignee: U.S. Spine, Inc., Salt Lake City, UT (US)

( * ) Notice: Subject to any disclaimer, the term of this patent is extended or adjusted under 35 U.S.C. 154(b) by 215 days.

(21) Appl. No.: 12/818,749

(22) Filed: Jun. 18, 2010

(65) Prior Publication Data

US 2011/0152948 A1 Jun. 23, 2011

Related U.S. Application Data

(60) Provisional application No. 61/218,574, filed on Jun. 19, 2009.

(51) Int. Cl.
*A61B 17/84* (2006.01)
*A61B 17/86* (2006.01)

(52) U.S. Cl. .......... 606/315; 606/305; 411/412

(58) Field of Classification Search .......... 411/411–412, 411/424; 606/301, 306, 315–318
See application file for complete search history.

(56) References Cited

U.S. PATENT DOCUMENTS

| | | | | |
|---|---|---|---|---|
| 4,027,573 A | * | 6/1977 | Laverty | 411/413 |
| 5,022,277 A | | 6/1991 | Shaffer | |
| 5,304,024 A | * | 4/1994 | Schuster | 411/418 |
| 5,591,029 A | * | 1/1997 | Zuest | 433/173 |
| 5,954,722 A | | 9/1999 | Bono | |
| 6,129,730 A | * | 10/2000 | Bono et al. | 606/291 |
| RE37,646 E | | 4/2002 | Zuest | |
| 7,063,701 B2 | | 6/2006 | Michelson | |
| 7,063,702 B2 | | 6/2006 | Michelson | |
| 7,179,260 B2 | | 2/2007 | Gerlach et al. | |
| 7,250,053 B2 | | 7/2007 | Orbay | |
| 7,282,053 B2 | | 10/2007 | Orbay | |
| 7,294,130 B2 | | 11/2007 | Orbay | |
| 7,582,107 B2 | | 9/2009 | Trail et al. | |
| 7,635,381 B2 | | 12/2009 | Orbay | |
| 2004/0006346 A1 | | 1/2004 | Holmen et al. | |
| 2004/0030339 A1 | | 2/2004 | Wach et al. | |
| 2004/0193155 A1 | | 9/2004 | Castaneda | |
| 2005/0033433 A1 | | 2/2005 | Michelson | |
| 2005/0107796 A1 | | 5/2005 | Gerlach et al. | |
| 2006/0052788 A1 | | 3/2006 | Thelen et al. | |
| 2006/0129151 A1 | | 6/2006 | Allen et al. | |
| 2006/0172258 A1 | | 8/2006 | Niznick | |
| 2007/0049938 A1 | | 3/2007 | Wallace et al. | |

(Continued)

FOREIGN PATENT DOCUMENTS

WO WO 02083015 A1 10/2002

*Primary Examiner* — Kevin T Truong
*Assistant Examiner* — Larry E Waggle, Jr.
(74) *Attorney, Agent, or Firm* — Phillips Ryther & Winchester; Matthew D. Thayne

(57) ABSTRACT

A pedicle screw assembly, including: a bone screw having a head portion and a thread portion, wherein the thread portion includes an axial shaft and a triple lead thread disposed about the axial shaft; and a rod retention member selectively coupled to the head portion of the bone screw. Optionally, the triple lead thread includes leads that originate at different points along the axial shaft. Optionally, the triple lead thread includes leads that terminate at different points along the axial shaft. Optionally, the axial shaft includes a first tapering portion proximate a tip of the axial shaft. Optionally, the axial shaft includes a second tapering portion proximate the tip of the axial shaft. Preferably, the second tapering portion tapers more steeply than the first tapering portion. Optionally, the axial shaft includes a reduced diameter portion proximate the head portion. Optionally, the axial shaft includes one or more tapering portions proximate the head portion.

19 Claims, 4 Drawing Sheets

U.S. PATENT DOCUMENTS

| | | |
|---|---|---|
| 2007/0049939 A1 | 3/2007 | Wallace et al. |
| 2007/0049940 A1 | 3/2007 | Wallace et al. |
| 2007/0055242 A1 | 3/2007 | Bailly |
| 2007/0123873 A1 | 5/2007 | Czartoski et al. |
| 2007/0123874 A1 | 5/2007 | Czartoski et al. |
| 2007/0123875 A1 | 5/2007 | Czartoski et al. |
| 2007/0123876 A1 | 5/2007 | Czartoski et al. |
| 2007/0142921 A1 | 6/2007 | Lewis et al. |
| 2007/0142922 A1 | 6/2007 | Lewis et al. |
| 2007/0162147 A1 | 7/2007 | Lewis et al. |
| 2007/0270846 A1 | 11/2007 | Metzinger |
| 2007/0276386 A1 | 11/2007 | Gerlach et al. |
| 2008/0292429 A1* | 11/2008 | Hasenbohler et al. ........ 411/413 |
| 2008/0300639 A1 | 12/2008 | Martin |
| 2009/0239195 A1* | 9/2009 | Wohrle et al. ................ 433/174 |
| 2010/0057138 A1 | 3/2010 | Murner et al. |
| 2010/0094352 A1* | 4/2010 | Iott et al. ....................... 606/301 |

* cited by examiner

TRIPLE LEAD BONE SCREW

CROSS-REFERENCE TO RELATED APPLICATION

The present non-provisional patent application/patent claims the benefit of priority of U.S. Provisional Patent Application No. 61/218,574, filed on Jun. 19, 2009, and entitled "TRIPLE LEAD BONE SCREW," the contents of which are incorporated in full by reference herein.

FIELD OF THE INVENTION

The present invention relates generally to a triple lead bone screw for use in surgical applications. More specifically, the present invention relates to a triple lead bone screw for use in spinal surgical applications, such as pedicle screw applications and the like.

BACKGROUND OF THE INVENTION

Triple lead screws are used in a variety of applications, including bone screw applications. These screws utilize three thread starts/leads between the distal end (i.e. tip) of the screw and the proximal end (i.e. head) of the screw. The three thread starts are typically spaced apart by about 120 degrees. The screws may be used to engage bone, or, more often, the triple lead portion is used to engage an anatomical plate or other implant structure. The advantage of triple lead screws relative to single or double lead screws is that triple lead screws are advanced farther with fewer turns, i.e. they are placed more quickly and with less effort. The disadvantage of triple lead screws relative to single or double lead screws is that triple lead screws typically have a lower pullout or backout strength, i.e. they may become dislodged more easily and with less effort.

What is still needed in the art is a triple lead pedicle screw or the like that overcomes the above mentioned disadvantage.

BRIEF SUMMARY OF THE INVENTION

In various exemplary embodiments, the present invention provides a triple lead pedicle screw or the like that is capable of being placed quickly with minimal effort and that resists pullout or backout at least as effectively as comparable single or double lead screws. This triple lead bone screw is ideally suited for the surgical correction of spinal deformities and other similar surgical procedures in which multiple screws must be placed. In such surgical procedures, a surgeon may become fatigued and time is of the essence.

In one exemplary embodiment, the present invention provides a pedicle screw assembly, including: a bone screw having a head portion and a thread portion, wherein the thread portion includes an axial shaft and a triple lead thread disposed about the axial shaft; and a rod retention member selectively coupled to the head portion of the bone screw. Optionally, the triple lead thread of the thread portion of the bone screw includes leads that start with about 120 degrees of separation. Optionally, the triple lead thread of the thread portion of the bone screw includes leads that originate at different points along the axial shaft of the thread portion of the bone screw. Optionally, the triple lead thread of the thread portion of the bone screw includes leads that terminate at different points along the axial shaft of the thread portion of the bone screw. Optionally, the axial shaft of the thread portion of the bone screw includes a first tapering portion proximate a tip of the axial shaft of the thread portion of the bone screw. Optionally, the axial shaft of the thread portion of the bone screw includes a second tapering portion proximate the tip of the axial shaft of the thread portion of the bone screw. Preferably, the second tapering portion tapers more steeply than the first tapering portion. Optionally, the axial shaft of the thread portion of the bone screw includes a reduced diameter portion proximate the head portion of the bone screw. Optionally, the axial shaft of the thread portion of the bone screw includes one or more tapering portions proximate the head portion of the bone screw. Preferably, the rod retention member is selectively pivotably coupled to the head portion of the bone screw.

In another exemplary embodiment, the present invention provides a bone screw, including: a head portion; and a thread portion, wherein the thread portion includes an axial shaft and a triple lead thread disposed about the axial shaft. Optionally, the triple lead thread of the thread portion of the bone screw includes leads that start with about 120 degrees of separation. Optionally, the triple lead thread of the thread portion of the bone screw includes leads that originate at different points along the axial shaft of the thread portion of the bone screw. Optionally, the triple lead thread of the thread portion of the bone screw includes leads that terminate at different points along the axial shaft of the thread portion of the bone screw. Optionally, the axial shaft of the thread portion of the bone screw includes a first tapering portion proximate a tip of the axial shaft of the thread portion of the bone screw. Optionally, the axial shaft of the thread portion of the bone screw includes a second tapering portion proximate the tip of the axial shaft of the thread portion of the bone screw. Preferably, the second tapering portion tapers more steeply than the first tapering portion. Optionally, the axial shaft of the thread portion of the bone screw includes a reduced diameter portion proximate the head portion of the bone screw. Optionally, the axial shaft of the thread portion of the bone screw includes one or more tapering portions proximate the head portion of the bone screw.

In a further exemplary embodiment, the present invention provides a bone screw, including: a head portion; and a thread portion, wherein the thread portion includes an axial shaft and a triple lead thread disposed about the axial shaft, wherein the axial shaft of the thread portion of the bone screw includes a first tapering portion proximate a tip of the axial shaft of the thread portion of the bone screw, and wherein the axial shaft of the thread portion of the bone screw includes a second tapering portion proximate the tip of the axial shaft of the thread portion of the bone screw, wherein the second tapering portion tapers more steeply than the first tapering portion. Optionally, the triple lead thread of the thread portion of the bone screw includes leads that originate at different points along the axial shaft of the thread portion of the bone screw. Optionally, the triple lead thread of the thread portion of the bone screw includes leads that terminate at different points along the axial shaft of the thread portion of the bone screw. Optionally, the axial shaft of the thread portion of the bone screw includes a reduced diameter portion proximate the head portion of the bone screw. Optionally, the axial shaft of the thread portion of the bone screw includes one or more tapering portions proximate the head portion of the bone screw.

BRIEF DESCRIPTION OF THE DRAWINGS

The present invention is illustrated and described herein with reference to the various drawings, in which like reference numbers are used to denote like screw components, as appropriate, and in which.

DETAILED DESCRIPTION OF THE INVENTION

Again, in various exemplary embodiments, the present invention provides a triple lead pedicle screw or the like that is capable of being placed quickly with minimal effort and that resists pullout or backout at least as effectively as comparable single or double lead screws. This triple lead bone screw is ideally suited for the surgical correction of spinal deformities/anomalies/trauma and other similar surgical procedures in which multiple screws must be placed. In such surgical procedures, a surgeon may be come fatigued and operative time is of the essence.

Figure 1:
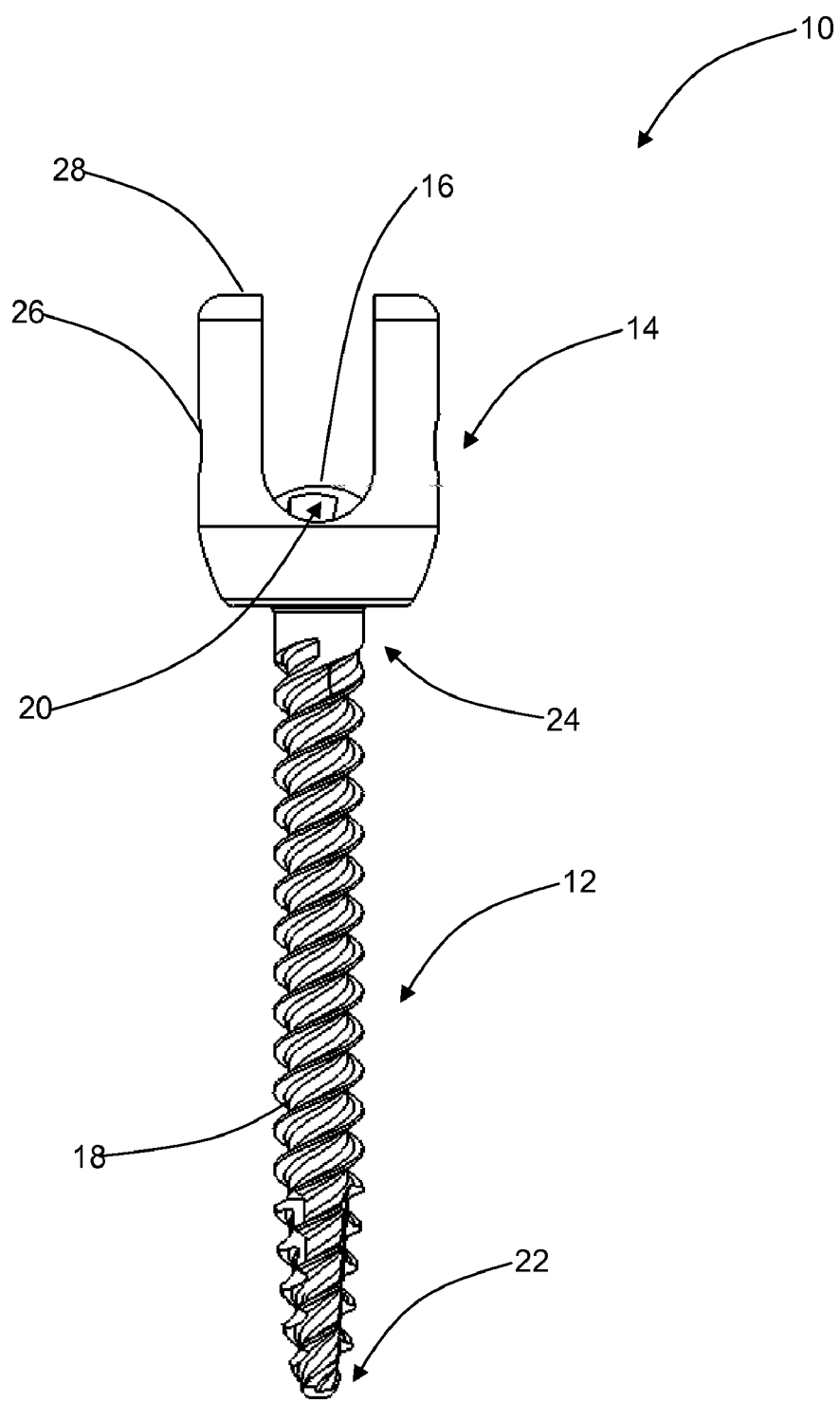
FIG. 1 is a planar side view of one exemplary embodiment of the triple lead pedicle screw assembly of the present invention, including the triple lead bone screw of the present invention and an associated rod retention member.
Figure 2:
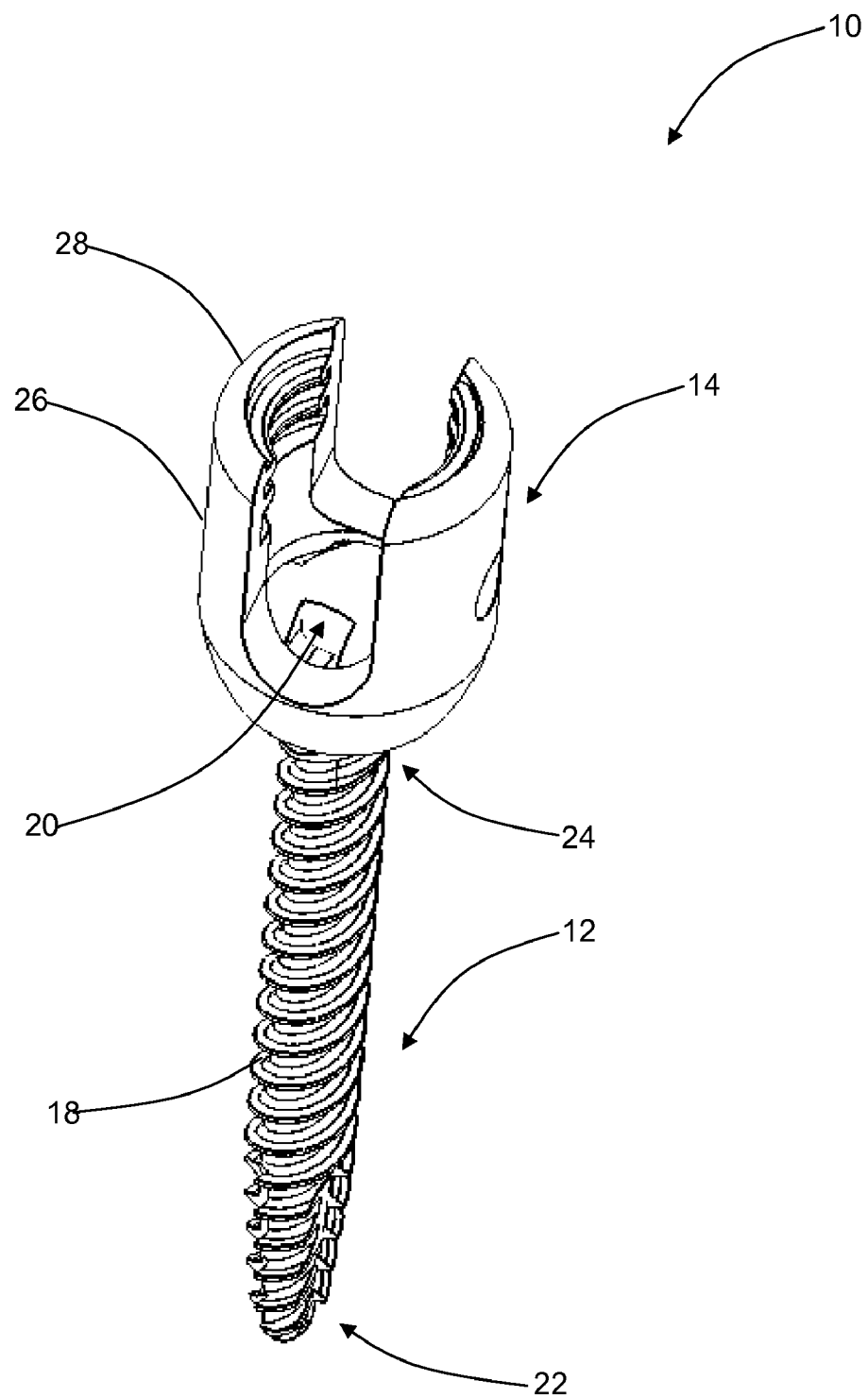
FIG. 2 is a perspective view of the triple lead pedicle screw assembly of FIG. 1.

Referring to FIGS. 1 and 2, in one exemplary embodiment, the triple lead pedicle screw assembly 10 of the present invention includes a triple lead bone screw 12 and a rod retention member 14.

The triple lead bone screw 12 includes a head portion 16 and a threaded portion 18. The head portion 16 of the triple lead bone screw 12 consists of an enlarged structure, such as a wholly or partially spherical structure, a wholly or partially cylindrical structure, or the like, having one or more tool receiving recesses 20 manufactured into the top surface thereof, by which the triple lead bone screw 12 is grasped and/or turned. Optionally, three such tool receiving recesses 20 are utilized and are spaced apart by about 120 degrees, although it will be readily apparent to those of ordinary skill in the art that other suitable configurations may be utilized. The threaded portion 18 of the triple lead bone screw 12 consists of three thread starts/leads between the distal end (i.e. tip) 22 of the screw 12 and the proximal end (i.e. head) 24 of the screw 12. Optionally, the three thread starts are spaced apart by about 120 degrees, although it will be readily apparent to those of ordinary skill in the art that other suitable configurations may be utilized. Optionally, the three thread starts/leads also originate and/or terminate at different positions along the length of the screw 12. In other words, the three thread starts/leads may or may not coincide along the length of the screw 12 and may be spaced apart by any desired constant or variable distance. Finally, one or more of the three thread starts/leads may be selectively broken or notched to create a biting surface, such as near the tip 22 of the screw 12 so that the screw will advance into bone from the first turn. Any suitable thickness, pitch, or other dimensions may be utilized, as well as any suitable materials (e.g. a biocompatible metal, ceramic, or plastic, bony material, etc.).

The rod retention member 14 consists of a U-shaped member 26 having a hole in the bottom. The threaded portion 18 of the bone screw 12 is disposed through this hole, with the head portion 16 of the bone screw being pivotably seated in the interior bottom of the U-shaped member, prior to the screw 12 being driven into bone. The rod retention member 14 includes a plurality of internally threaded, concentrically arranged, vertically extending arm members 28 between which a stabilizing rod or other similar stabilizing structure (not illustrated) is selectively disposed. This stabilizing rod is then "locked" into place via the engagement of an externally threaded cap (not illustrated) into the internal threads of the arm members 28, thereby "locking" the orientation of the rod retention member 14 with respect to the head portion 16 of the triple lead bone screw 12, as the stabilizing rod is in direct or indirect contact with the head portion 16 of the triple lead bone screw 12. It will be readily apparent to those of ordinary skill in the art that various other structures may also be disposed between the stabilizing rod and either or both of the externally threaded cap and the head portion 16 of the triple lead bone screw 12. In this manner, screws 12 may be placed in different anatomical structures, or different parts of the same anatomical structure, and securely joined by stabilizing structures in a predetermined configuration and alignment.

Figure 3:
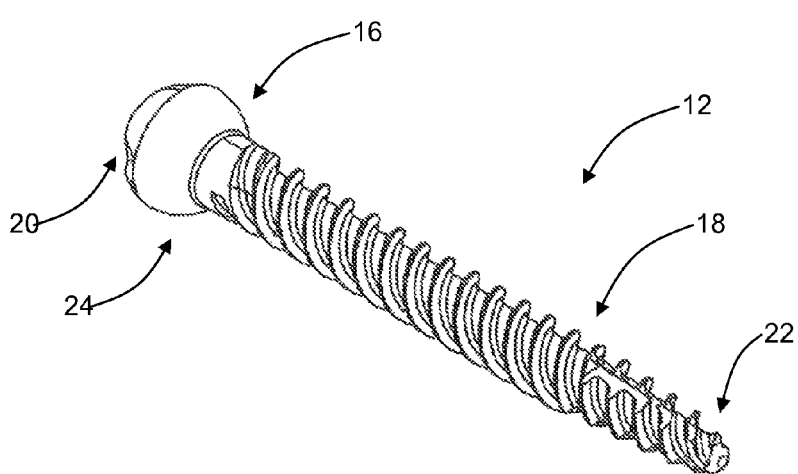
FIG. 3 is a perspective view of one exemplary embodiment of the bone screw of the present invention.
Figure 4:
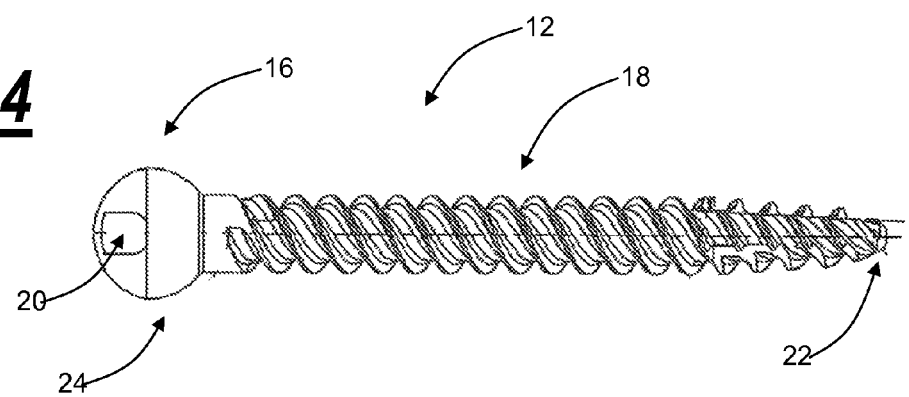
FIG. 4 is a planar side view of the bone screw of FIG. 3.
Figure 5:
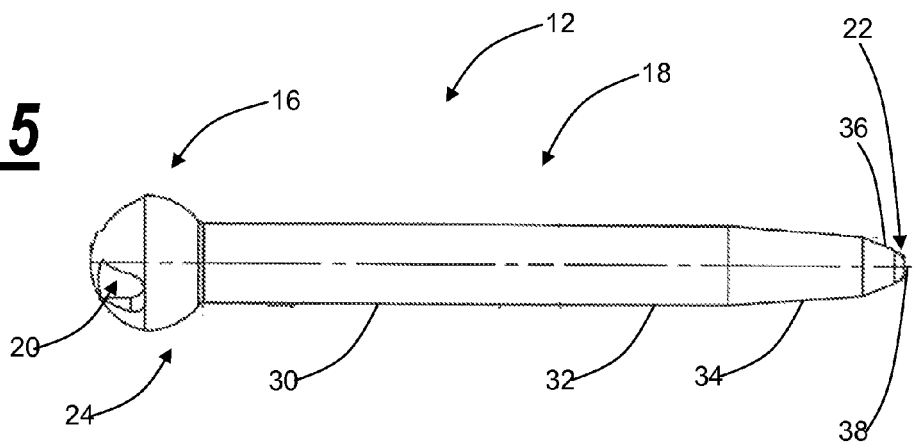
FIG. 5 is another planar side view of the bone screw of FIG. 3.

Referring to FIGS. 3-5, in one exemplary embodiment, the triple lead bone screw 12 of the present invention includes a head portion 16 and a threaded portion 18. The head portion 16 of the triple lead bone screw 12 consists of an enlarged structure, such as a wholly or partially spherical structure, a wholly or partially cylindrical structure, or the like, having one or more tool receiving recesses 20 manufactured into the top surface thereof, by which the triple lead bone screw 12 is grasped and/or turned. Optionally, three such tool receiving recesses 20 are utilized and are spaced apart by about 120 degrees, although it will be readily apparent to those of ordinary skill in the art that other suitable configurations may be utilized. The threaded portion 18 of the triple lead bone screw 12 consists of three thread starts/leads between the distal end (i.e. tip) 22 of the screw 12 and the proximal end (i.e. head) 24 of the screw 12. Optionally, the three thread starts are spaced apart by about 120 degrees, although it will be readily apparent to those of ordinary skill in the art that other suitable configurations may be utilized. Optionally, the three thread starts/leads also originate and/or terminate at different positions along the length of the screw 12. In other words, the three thread starts/leads may or may not coincide along the length of the screw 12 and may be spaced apart by any desired constant or variable distance. Finally, one or more of the three thread starts/leads may be selectively broken or notched to create a biting surface, such as near the tip 22 of the screw 12 so that the screw will advance into bone from the first turn. Any suitable thickness, pitch, or other dimensions may be utilized, as well as any suitable materials (e.g. a biocompatible metal, ceramic, or plastic, bony material, etc.).

Referring specifically to FIG. 5, the threaded portion 18 of the screw 12 includes an axial shaft 30 that may have a non-tapering portion 32, a first tapering portion 34, and a second tapering portion 36 disposed, in order, between the head portion 16 of the screw 12 and the rounded or pointed tip 38 of the screw 12. Preferably, the taper of the second tapering portion 36 is greater than the taper of the first tapering portion 34, with the second tapering portion sweeping a 45-degree arc, a 60-degree arc, etc. The threads are disposed about these various segments of the screw 12.

Figure 6:
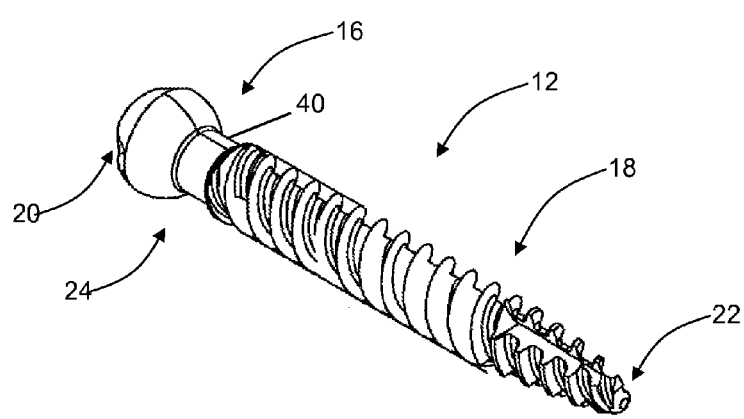
FIG. 6 is a perspective view of another exemplary embodiment of the bone screw of the present invention.
Figure 7:
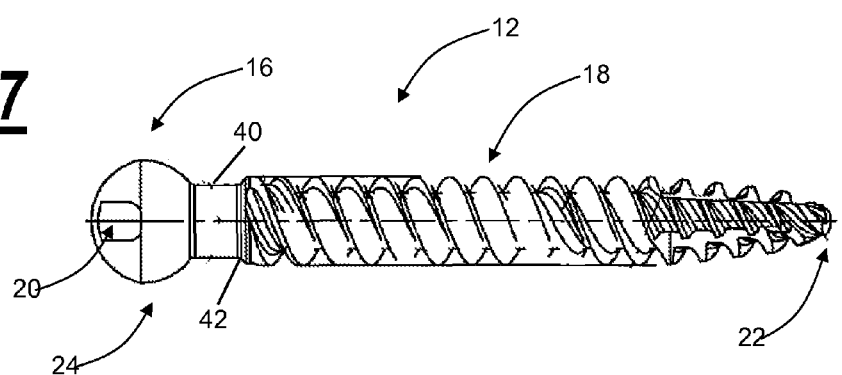
FIG. 7 is a planar side view of the bone screw of FIG. 6.
Figure 8:
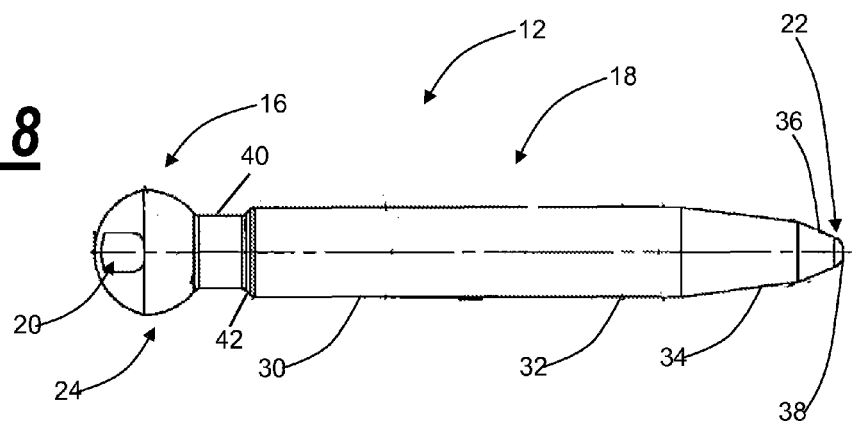
FIG. 8 is another planar side view of the bone screw of FIG. 6.

Referring to FIGS. 6-8, in another exemplary embodiment, the triple lead bone screw 12 of the present invention includes a head portion 16 and a threaded portion 18. The head portion 16 of the triple lead bone screw 12 consists of an enlarged structure, such as a wholly or partially spherical structure, a wholly or partially cylindrical structure, or the like, having one or more tool receiving recesses 20 manufactured into the top surface thereof, by which the triple lead bone screw 12 is grasped and/or turned. Optionally, three such tool receiving recesses 20 are utilized and are spaced apart by about 120 degrees, although it will be readily apparent to those of ordinary skill in the art that other suitable configurations may be utilized. The threaded portion 18 of the triple lead bone screw 12 consists of three thread starts/leads between the distal end (i.e. tip) 22 of the screw 12 and the proximal end (i.e. head) 24 of the screw 12. Optionally, the three thread starts are spaced apart by about 120 degrees, although it will be readily apparent to those of ordinary skill in the art that other suitable configurations may be utilized. Optionally, the three thread starts/leads also originate and/or terminate at different positions along the length of the screw 12. In other words, the three thread starts/leads may or may not coincide along the length of the screw 12 and may be spaced apart by any desired constant or variable distance. Finally, one or more of the three thread starts/leads may be selectively broken or notched to create a biting surface, such as near the tip 22 of the screw 12 so that the screw will advance into bone from the first turn. Any suitable thickness, pitch, or other dimensions may be utilized, as well as any suitable materials (e.g. a biocompatible metal, ceramic, or plastic, bony material, etc.).

Referring specifically to FIG. 8, the threaded portion 18 of the screw 12 includes an axial shaft 30 that may have a non-tapering portion 32, a first tapering portion 34, and a second tapering portion 36 disposed, in order, between the head portion 16 of the screw 12 and the rounded or pointed tip 38 of the screw 12. Preferably, the taper of the second tapering portion 36 is greater than the taper of the first tapering portion 34, with the second tapering portion sweeping a 45-degree arc, a 60-degree arc, etc. The threads are disposed about these various segments of the screw 12. In this exemplary embodiment, a reduced diameter portion 40 and one or more tapering portions 42 are also disposed along the axial shaft 30 between the head portion 16 and the threaded portion 18 of the screw 12.

Axial pullout testing of the triple lead bone screw 12 of the present invention demonstrated performance comparable to that of a conventional single lead bone screw.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

The invention claimed is:

1. A pedicle screw assembly, comprising:
a bone screw comprising a head portion and a thread portion, wherein the thread portion comprises an axial shaft and a triple lead thread disposed about the axial shaft, wherein the triple lead thread comprises three thread leads, wherein the axial shaft of the thread portion of the bone screw comprises a first tapering portion, wherein each of the three leads extend coextensively along at least a portion of the first tapering portion, wherein the axial shaft of the thread portion of the bone screw comprises a second tapering portion proximate a tip of the axial shaft of the thread portion of the bone screw, wherein each of the three leads extend coextensively along at least a portion of the second tapering portion, and wherein the second tapering portion tapers more steeply than the first tapering portion; and
a rod retention member selectively coupled to the head portion of the bone screw.

2. The pedicle screw assembly of claim 1, wherein the triple lead thread of the thread portion of the bone screw comprises leads that start with about 120 degrees of separation.

3. The pedicle screw assembly of claim 1, wherein the triple lead thread of the thread portion of the bone screw comprises leads that originate at different points along the axial shaft of the thread portion of the bone screw.

4. The pedicle screw assembly of claim 1, wherein the triple lead thread of the thread portion of the bone screw comprises leads that terminate at different points along the axial shaft of the thread portion of the bone screw.

5. The pedicle screw assembly of claim 1, wherein the axial shaft of the thread portion of the bone screw comprises a reduced diameter portion proximate the head portion of the bone screw.

6. The pedicle screw assembly of claim 1, wherein the axial shaft of the thread portion of the bone screw comprises one or more tapering portions proximate the head portion of the bone screw.

7. The pedicle screw assembly of claim 1, wherein the rod retention member is selectively pivotably coupled to the head portion of the bone screw.

8. A bone screw, comprising:
a head portion; and
a thread portion, wherein the thread portion comprises an axial shaft and a triple lead thread disposed about the axial shaft, wherein the triple lead thread comprises three thread leads, wherein each of the three leads extends coextensively along at least substantially the entire length of the axial shaft, wherein each of the three leads originate adjacent to the head portion along a non-tapering portion of the thread portion, and wherein each of the three leads terminate at different points adjacent to one another along the axial shaft of the thread portion of the bone screw adjacent to a tip of the axial shaft.

9. The bone screw of claim 8, wherein the triple lead thread of the thread portion of the bone screw comprises leads that start with about 120 degrees of separation.

10. The bone screw of claim 8, wherein the triple lead thread of the thread portion of the bone screw comprises leads that originate at different points along the axial shaft of the thread portion of the bone screw.

11. The bone screw of claim 8, wherein the axial shaft of the thread portion of the bone screw comprises a first tapering portion.

12. The bone screw of claim 11, wherein the axial shaft of the thread portion of the bone screw comprises a second tapering portion proximate the tip of the axial shaft of the thread portion of the bone screw.

13. The bone screw of claim 12, wherein the second tapering portion tapers more steeply than the first tapering portion.

14. The bone screw of claim 8, wherein the axial shaft of the thread portion of the bone screw comprises a reduced diameter portion proximate the head portion of the bone screw.

15. The bone screw of claim 8, wherein the axial shaft of the thread portion of the bone screw comprises one or more tapering portions proximate the head portion of the bone screw.

16. A bone screw, comprising:
a head portion; and
a thread portion, wherein the thread portion comprises an axial shaft and a triple lead thread disposed about the axial shaft comprising three thread leads, wherein the axial shaft of the thread portion of the bone screw comprises a first tapering portion, wherein each of the three leads extend coextensively along at least a portion of the first tapering portion, wherein the axial shaft of the thread portion of the bone screw comprises a second tapering portion proximate a tip of the axial shaft of the thread portion of the bone screw, wherein each of the three leads extend coextensively along at least a portion of the second tapering portion, wherein the triple lead thread of the thread portion of the bone screw comprises leads that originate at different points along the axial shaft of the thread portion of the bone screw, and wherein the second tapering portion tapers more steeply than the first tapering portion.

17. The bone screw of claim 16, wherein the triple lead thread of the thread portion of the bone screw comprises leads that terminate at different points along the axial shaft of the thread portion of the bone screw.

18. The bone screw of claim 16, wherein the axial shaft of the thread portion of the bone screw comprises a reduced diameter portion proximate the head portion of the bone screw.

19. The bone screw of claim 16, wherein the axial shaft of the thread portion of the bone screw comprises one or more tapering portions proximate the head portion of the bone screw.

* * * * *